US012618024B2

(12) United States Patent
Liu

(10) Patent No.: US 12,618,024 B2
(45) Date of Patent: May 5, 2026

(54) MICROCELL SYSTEMS FOR CONTROLLED RELEASE OF FRAGRANCES

(71) Applicant: E INK CORPORATION, Billerica, MA (US)

(72) Inventor: Lei Liu, Fremont, CA (US)

(73) Assignee: E INK CORPORATION, Billerica, MA (US)

( * ) Notice: Subject to any disclaimer, the term of this patent is extended or adjusted under 35 U.S.C. 154(b) by 600 days.

(21) Appl. No.: 18/068,705

(22) Filed: Dec. 20, 2022

(65) Prior Publication Data

US 2023/0212484 A1    Jul. 6, 2023

Related U.S. Application Data

(60) Provisional application No. 63/295,961, filed on Jan. 3, 2022.

(51) Int. Cl.
| | |
|---|---|
| *C11D 3/50* | (2006.01) |
| *A61K 8/02* | (2006.01) |
| *A61Q 13/00* | (2006.01) |

(52) U.S. Cl.
CPC ............ *C11D 3/505* (2013.01); *A61K 8/0279* (2013.01); *A61Q 13/00* (2013.01); *A61K 2800/56* (2013.01)

(58) Field of Classification Search
CPC ................ A61K 8/0279; A61K 8/0216; A61K 2800/56; C11D 3/505; A61Q 13/00
USPC ........................................................... 512/1
See application file for complete search history.

(56) References Cited

U.S. PATENT DOCUMENTS

| | | | |
|---|---|---|---|
| 5,261,169 A | 11/1993 | Willford |
| 5,395,047 A | 3/1995 | Pendergrass, Jr. |
| 5,455,043 A | 10/1995 | Fischel-Ghodsian |
| 6,933,098 B2 | 8/2005 | Chan-Park et al. |
| 7,715,088 B2 | 5/2010 | Liang et al. |
| 8,178,114 B2 | 5/2012 | Klausen et al. |
| 9,220,664 B1 | 12/2015 | Jhin et al. |
| 10,087,344 B2 | 10/2018 | Moran |
| 2010/0047511 A1 | 2/2010 | Gannon et al. |
| 2010/0075561 A1 | 3/2010 | Burrow et al. |
| 2010/0314461 A1 | 12/2010 | Gruenbacher et al. |
| 2014/0021269 A1 | 1/2014 | Roreger et al. |
| 2017/0136139 A1 | 5/2017 | Seshadri et al. |
| 2018/0028776 A1 | 2/2018 | Clark |
| 2018/0104372 A1 | 4/2018 | McGlade et al. |
| 2019/0142763 A1 | 5/2019 | Liu |
| 2020/0069832 A1 | 3/2020 | Santini et al. |
| 2020/0306404 A1 | 10/2020 | Seshadri et al. |

FOREIGN PATENT DOCUMENTS

| | | | | |
|---|---|---|---|---|
| WO | WO-2019099323 A1 * | 5/2019 | ............. | A61K 47/34 |
| WO | 2020089916 A1 | 5/2020 | | |

OTHER PUBLICATIONS

Korean Intellectual Property Office, "International Search Report and Written Opinion", PCT/US2022/082000, Apr. 26, 2023. Apr. 26, 2023.

Harvey, T.G.; "Replication techniques for micro-optics"; SPIE Proc. vol. 3099, pp. 76-82; 1997. Jan. 1, 1997.

European Patent Office, "Extended European Search Report", EP Appl. No. 22917462.8, Dec. 5, 2025.

* cited by examiner

*Primary Examiner* — Jessica Whiteley
(74) *Attorney, Agent, or Firm* — Quarles & Brady, LLP

(57) ABSTRACT

A fragrance delivery system is disclosed whereby multiple fragrances can be released on demand. The fragrance delivery system includes a plurality of microcells, wherein each of the plurality of microcells is filled with a fragrance composition. Each of the plurality of microcells includes an opening, the opening being spanned by a porous sealing layer. The fragrance delivery system provides a tool to deliver a customizable olfactory effect in the vicinity of the fragrance delivery system.

20 Claims, 11 Drawing Sheets

1000

1004

1003

1002

1001

UV OR LIGHT 1205  1204

1206

1200

1201a

1202

1203

1200

1207

1201c

1201b

1202

1203

UV OR LIGHT

1200

1206

1204

1205

1201a

1202

1203

UV OR LIGHT

1200

1207

1201b

1202

1203

MICROCELL SYSTEMS FOR CONTROLLED RELEASE OF FRAGRANCES

RELATED APPLICATIONS

This application claims priority to U.S. Provisional Patent Application No. 63/295,961 filed on Jan. 3, 2022, which is incorporated by reference in its entirety, along with all other patents and patent applications disclosed herein.

BACKGROUND

The development of methodologies for controlled and extended release of benefit agents have attracted significant attention during the last decades. This is true for a large variety of benefit agents including pharmaceutical, nutraceutical agents, agricultural nutrients and related substances, cosmetic agents, fragrances, air care agents, biocides, fertilizers, and many other benefit agents in a variety of fields. Controlled and extended release delivery systems may involve the delivery of various benefit agents in different forms, such as solid, liquid and gas, to different locations, and under different conditions.

A variety of delivery systems has been developed during the last decades that provide on demand delivery of benefit agents. For instance, Chrono Therapeutics (Hayward, CA) has tested a micro pump-enabled smart transdermal patch for delivering nicotine. Nonetheless, the corresponding device is large and visible through clothing as a sizeable bump. Thus, there remains a need for small, simple, inexpensive, versatile and safe delivery systems for delivering benefit agents on demand.

Delivery systems for fragrances are commercially available. For example, systems that refresh spaces comprise materials that absorb fragrances. Such absorbing materials include cotton, gels, and microporous films. These products release fragrances in spaces over time. However, delivery of more than one fragrances in a controlled manner from the same system is challenging. The inventors of the present invention surprisingly found that a microcell device having a porous layer could deliver multiple fragrances from the same system at a controlled manner, providing a customizable odor over a period of time.

SUMMARY OF THE INVENTION

The invention of the present application addresses the need of controlled release of fragrances by providing a delivery system whereby a fragrance can be released on demand. Additionally, as described below, the invention provides a system for delivering varying amounts of fragrances from the same delivery system at different times and controlled rates, and for delivering multiple fragrances at the same or different times from the same delivery system in controlled rates.

In one aspect, the invention is a fragrance delivery system comprising a backing layer, a microcell layer, a porous sealing layer, and a first release sheet. The microcell layer comprises a plurality of microcells. Each microcell of the plurality of microcells has an opening. The porous sealing layer spans the opening of the plurality of microcells. The porous sealing layer has an average pores size, the average pore size being from 0.2 nm to 1 mm. The porous sealing layer comprises a plurality of sealing slices, each sealing slice being independently removable or retractable. The plurality of microcells comprises a plurality of first type of microcells, each microcell of the plurality of first type of microcells comprising a composition of a first fragrance having a first concentration of the first fragrance. The composition of the first fragrance may comprise a first aqueous carrier or a first non-aqueous carrier. The composition of the first fragrance may be a liquid or a gel.

The plurality of microcells may comprise a plurality of second type of microcells and a plurality of third type of microcells. Portions of the porous sealing layer span the openings of the plurality of second type of microcells. Portions of the porous sealing layer span the openings of the plurality of third type of microcells. The portions of the porous sealing layer spanning the openings of the plurality of second type of microcells have a second thickness. The portions of the porous sealing layer spanning the openings of the plurality of third type of microcells have a third thickness. The second thickness may be different from the third thickness. The plurality of microcells may further comprise a plurality of fourth type of microcells. Portions of the porous sealing layer span the openings of the plurality of fourth type of microcells. The portions of the porous sealing layer spanning the openings of the plurality of fourth type of microcells have a fourth thickness. The fourth thickness may be different from the second thickness and the third thicknesses.

The plurality of microcells may comprise a plurality of fifth type of microcells and a plurality of sixth type of microcells. Portions of the porous sealing layer span the openings of the plurality of fifth type of microcells. Portions of the porous sealing layer span the openings of the plurality of sixth type of microcells. The portions of the porous sealing layer spanning the openings of the plurality of fifth type of microcells may have a fifth average pore size. The portions of the porous sealing layer spanning the openings of the plurality of sixth type of microcells may have a sixth average pore size. The fifth average pore size may be different from the sixth average pore size. The plurality of microcells may further comprise a plurality of seventh type of microcells. Portions of the porous sealing layer span the openings of the plurality of seventh type of microcells. The portions of the porous sealing layer spanning the openings of the plurality of seventh type of microcells may have a seventh average pore size. The seventh average pore size may be different from the fifth and the sixth average pore sizes.

The plurality of microcells may comprise a plurality of eighth type of microcells and a plurality of ninth type of microcells. Each microcell of the eighth type of microcells may have an eighth volume. Each microcell of the ninth type of microcells may have a ninth volume. The eighth volume may be different from the ninth volume. The plurality of microcells may further comprise a plurality of tenth type of microcells. Each microcell of the tenth type of microcells may have a tenth volume. The tenth volume may be different from the eighth and ninth volumes.

The plurality of microcells may comprise a plurality of eleventh type of microcells and a plurality of twelfth type of microcells. Each microcell of the eleventh type of microcells may have an eleventh concentration of the first fragrance. Each microcell of the twelfth type of microcells may have a twelfth concentration of the first fragrance. The eleventh concentration may be different from the twelfth concentration.

The plurality of microcells may further comprise a plurality of thirteenth type of microcells. Each microcell of the plurality of thirteenth type of microcells comprises a composition of a second fragrance. The second fragrance is different from the first fragrance. The plurality of microcells may further comprise a plurality of fourteenth type of microcells. Each microcell of the plurality of fourteenth type of microcells comprises a composition of a third fragrance. The third fragrance may be different from the first fragrance and the second fragrance.

The release sheet of the fragrance delivery system may comprise a plurality of release sheet slices, each release sheet slice being independently removable or retractable.

The fragrance delivery system may comprise a top coating layer. The top coating layer may be disposed between the porous sealing layer and the release sheet. The top coating layer may have average pore size of less than 0.2 nm. The top coating layer may have average pore size larger than 0.2 nm. The average pore size of the top coating layer is smaller than the average pore size of the porous sealing layer. The top coating layer may comprise a plurality of top coating slices, each top coating slice being independently removable or retractable.

The fragrance delivery system may further comprise an adhesive layer adjacent the backing layer, the backing layer being disposed between the adhesive layer and the microcell layer.

The fragrance delivery system may further comprise a second release sheet adjacent to the adhesive layer, the adhesive layer being disposed between the second release sheet and the backing layer.

In another aspect, the invention is a method of delivering fragrances form a fragrance delivery system, the fragrance delivery system comprising (a) a backing layer; (b) a microcell layer comprising a plurality of microcells, each microcell of the plurality of microcells having an opening, the plurality of microcells comprising a plurality of first type of microcells, each microcell of the plurality of first type of microcells comprises a composition of a first fragrance having a first concentration of the first fragrance; (c) a porous sealing layer scanning the opening of the plurality of microcells, the porous sealing layer having average pore size of 0.2 nm to 1 mm, the porous sealing layer comprising a plurality of sealing slices, each sealing slice being independently removable or retractable; (d) a top coating layer, the top coating layer having average pore size larger than 0.1 nm, the top coating layer comprising a plurality of top coating slices, each top coating slice being independently removable or retractable; (e) a first release sheet comprising a plurality of release sheet slices, each release sheet slice being independently removable or retractable; the method comprising: (1) removing or retracting the release sheet or one or more release sheet slices; (2) removing or retracting the top coating layer or one or more top coating slices; and (3) removing or retracting the sealing layer or one or more sealing slices.

The method of delivering fragrances may further comprise a step (4) re-attaching the sealing layer or one or more sealing slices. The method of delivering fragrances may further comprise a step (5) re-attaching the top coating layer or one or more top coating slices. The method of delivering fragrances may further comprise a step (6) re-attaching the release sheet or one or more release sheet slices.

4

Figure 2:
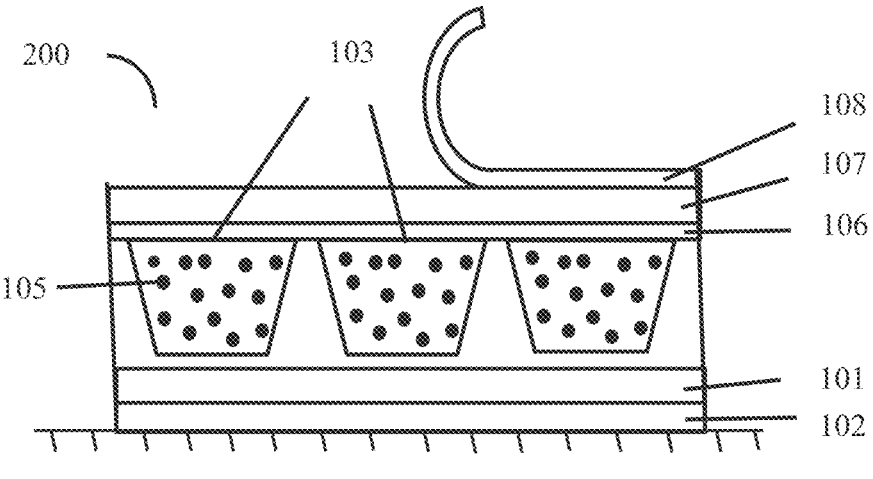

FIG. 2 illustrates a side view of an example of the fragrance delivery system of the present invention that is being activated by removing the release sheet or part of the release sheet.

Figure 3A:
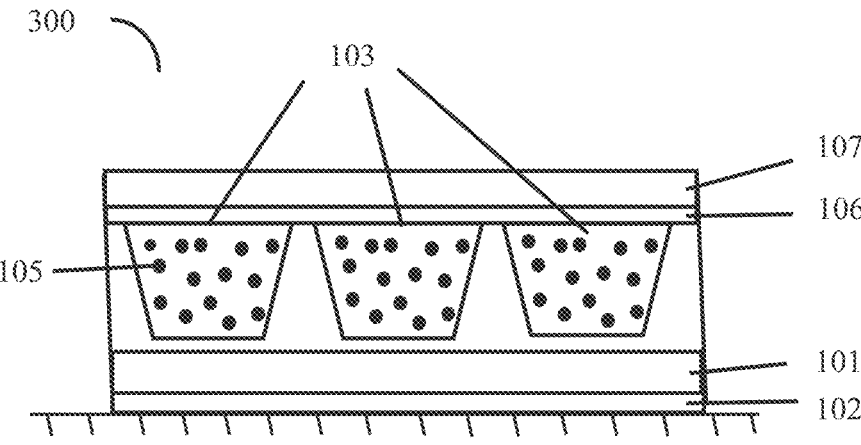

FIG. 3A illustrates a side view of an example of the fragrance delivery system of the present invention that has been activated by the removal of the release sheet.

Figure 3B:
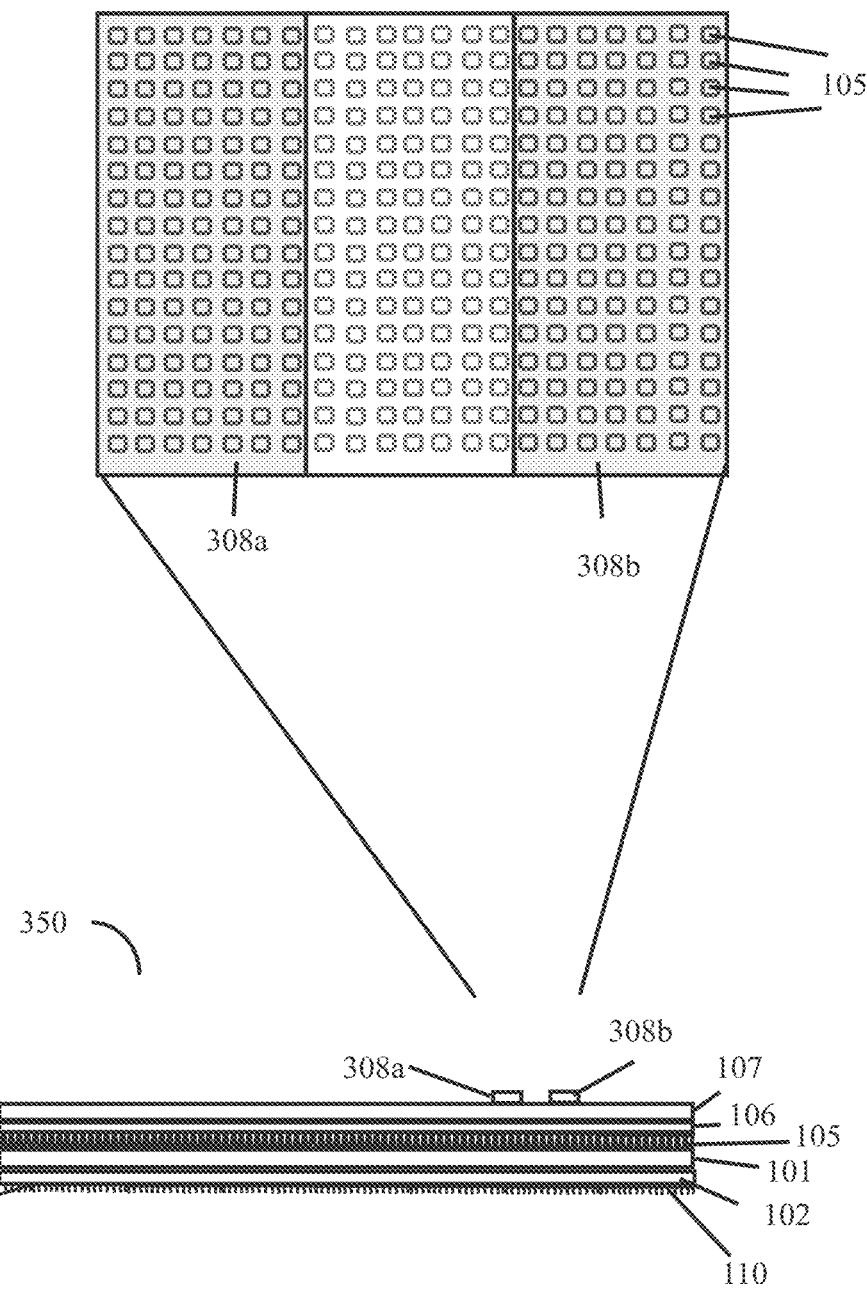

FIG. 3B illustrates a side view and a partial view from above of an example of the fragrance delivery system of the present invention that has been activated; the fragrance delivery system comprises two release sheet slices.

Figure 4:
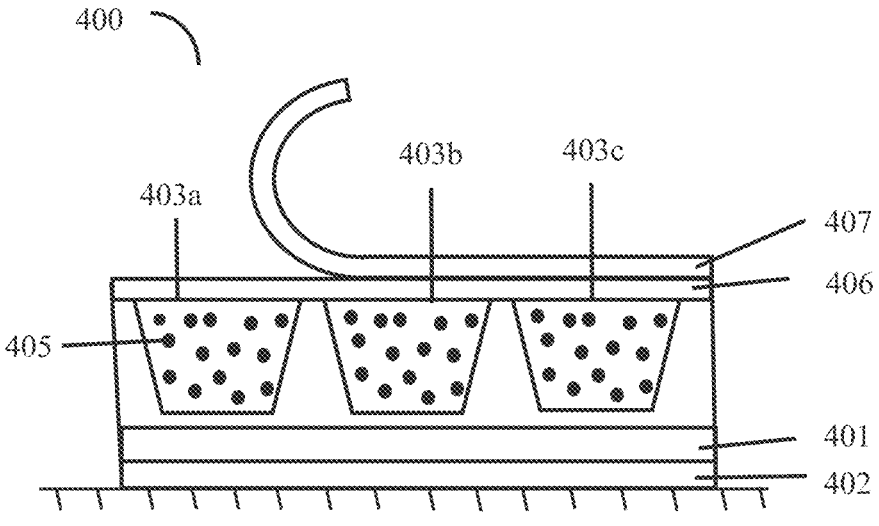

FIG. 4 illustrates a side view of an example of the fragrance delivery system of the present invention having a top coating layer partially removed.

Figure 5:
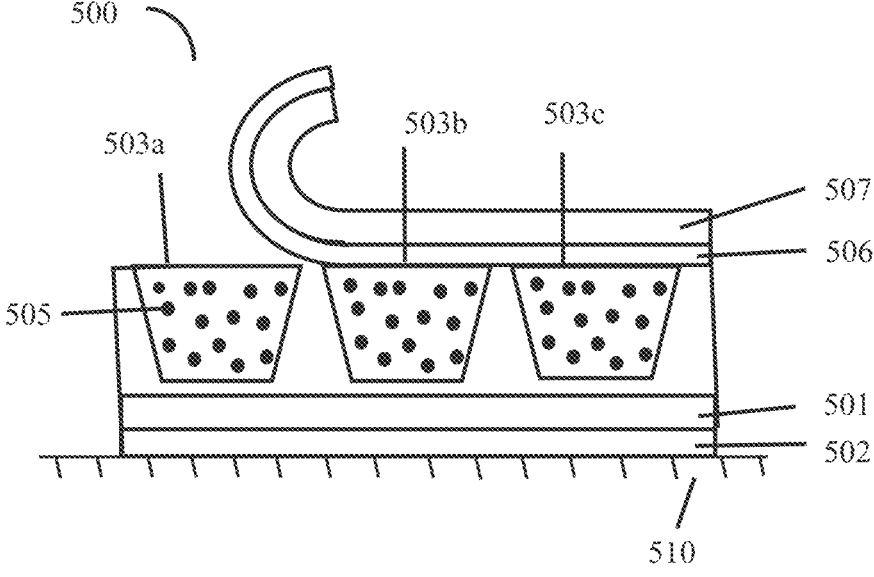

FIG. 5 illustrates a side view of an example of the fragrance delivery system of the present invention having the sealing layer and the top coating layer partially removed.

Figure 6:
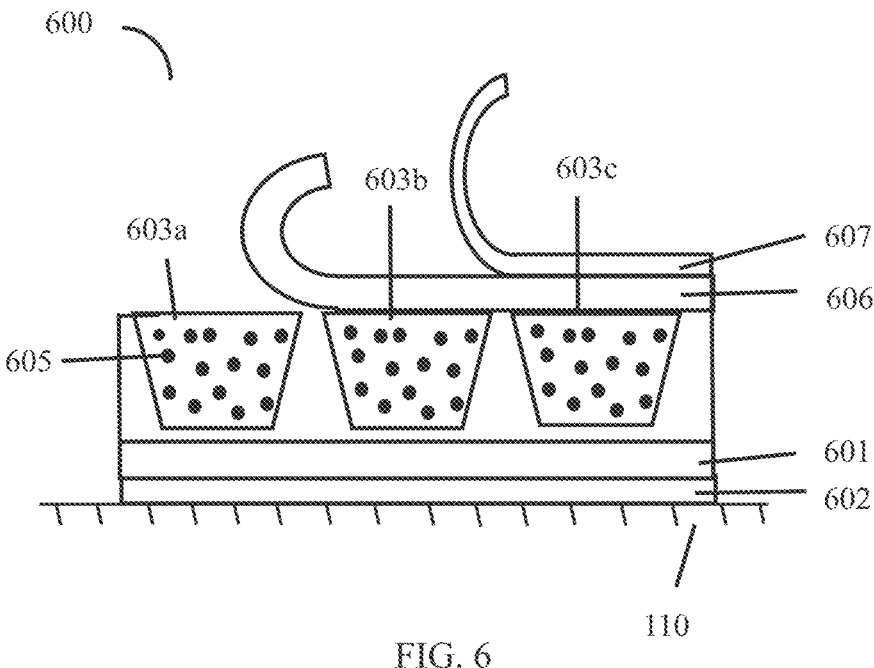

FIG. 6 illustrates a side view of an example of the fragrance delivery system of the present invention having microcells activated; a microcell is open, a microcell having the top coating removed, and a microcell still having a sealing layer and a top coating layer.

Figure 7:
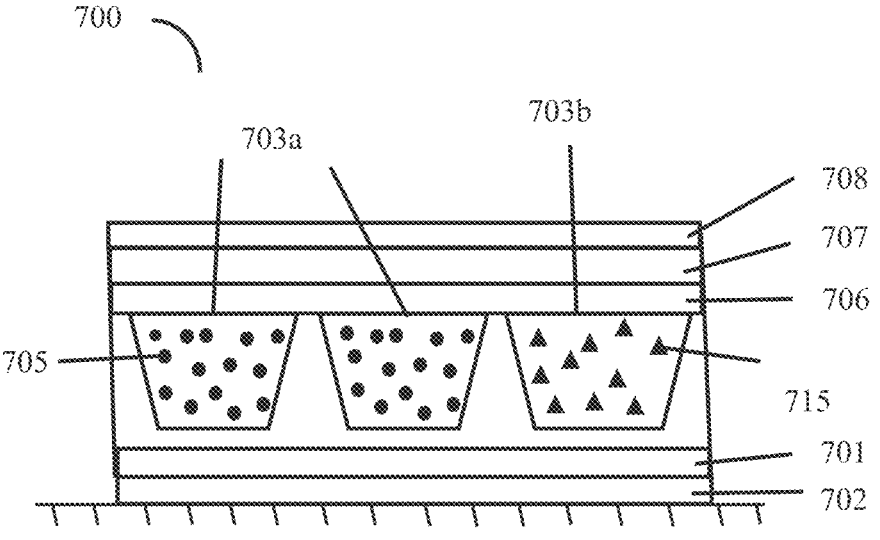

FIG. 7 illustrates a side view of an example of the fragrance delivery system of the present invention that is not activated; the fragrance delivery system comprises microcells comprising a first fragrance, and microcells comprising a second fragrance.

Figure 8:
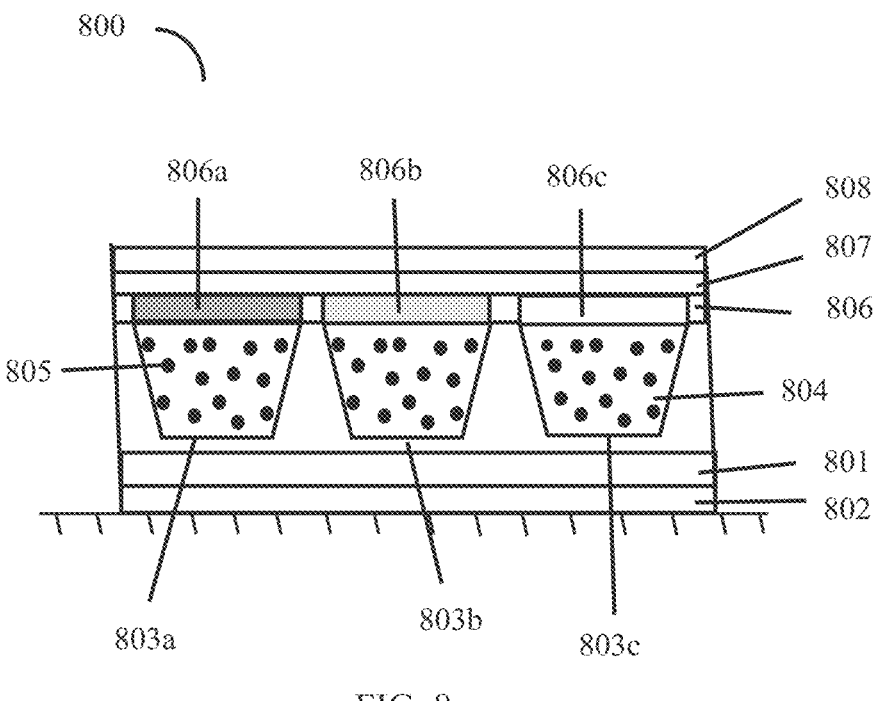

FIG. 8 illustrates a side view of an example of the fragrance delivery system of the present invention that is not activated; the fragrance delivery system comprises microcells of three types that have sealing layers of different average pore sizes.

Figure 9:
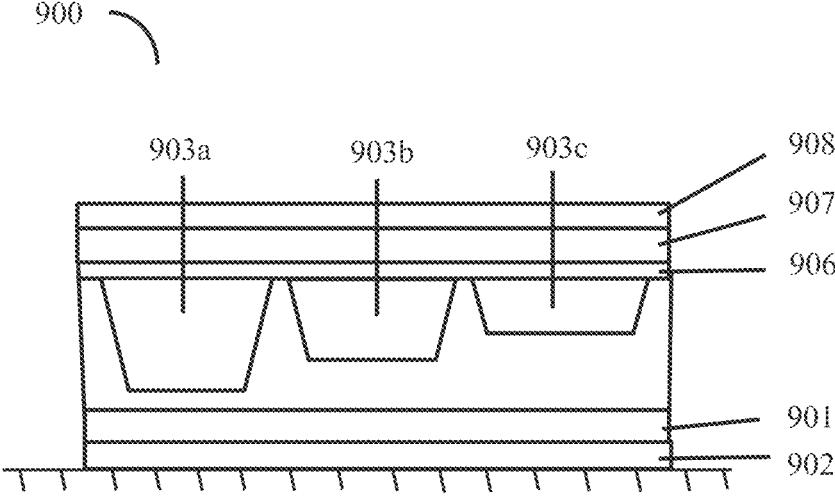

FIG. 9 illustrates a side view of an example of the fragrance delivery system of the present invention that is not activated; the fragrance delivery system comprises microcells of three types that have different volumes.

Figure 10:
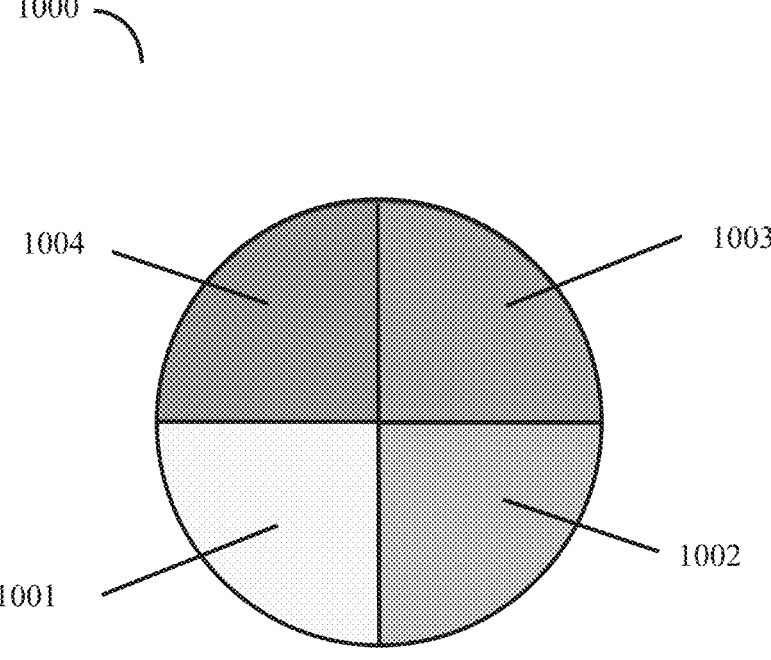

FIG. 10 illustrates a top view of an example of the fragrance delivery system of the present invention that comprise four microcell types, each type comprising a different fragrance.

Figure 11:
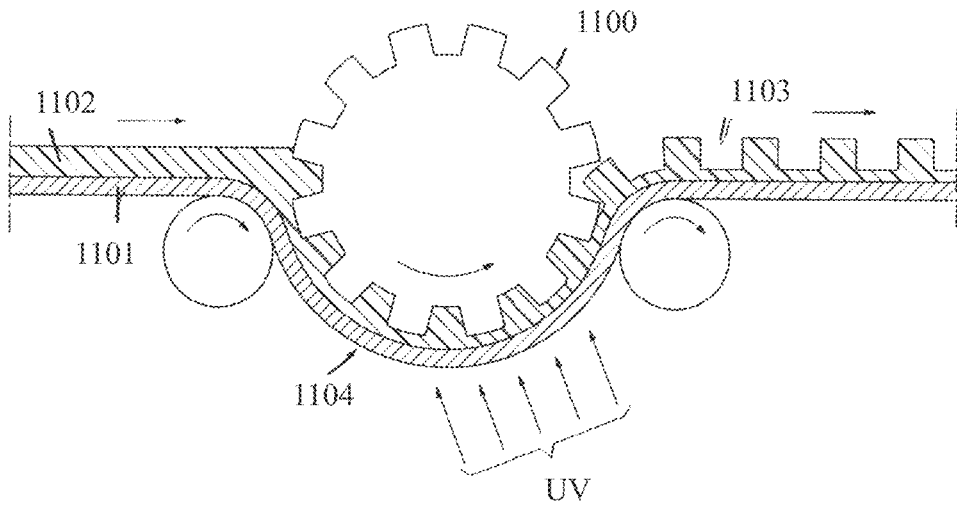

FIG. 11 shows a method for making microcells for the present invention using a roll-to-roll process.

Figures 12A, 12B:
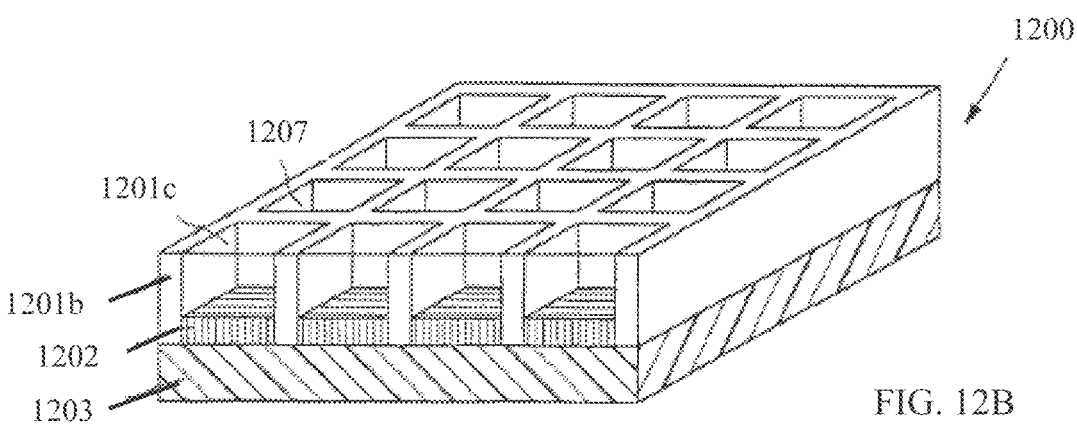

FIGS. 12A and 12B detail the production of microcells for a fragrance delivery system using photolithographic exposure through a photomask of a conductor film coated with a thermoset precursor.

Figure 12C:
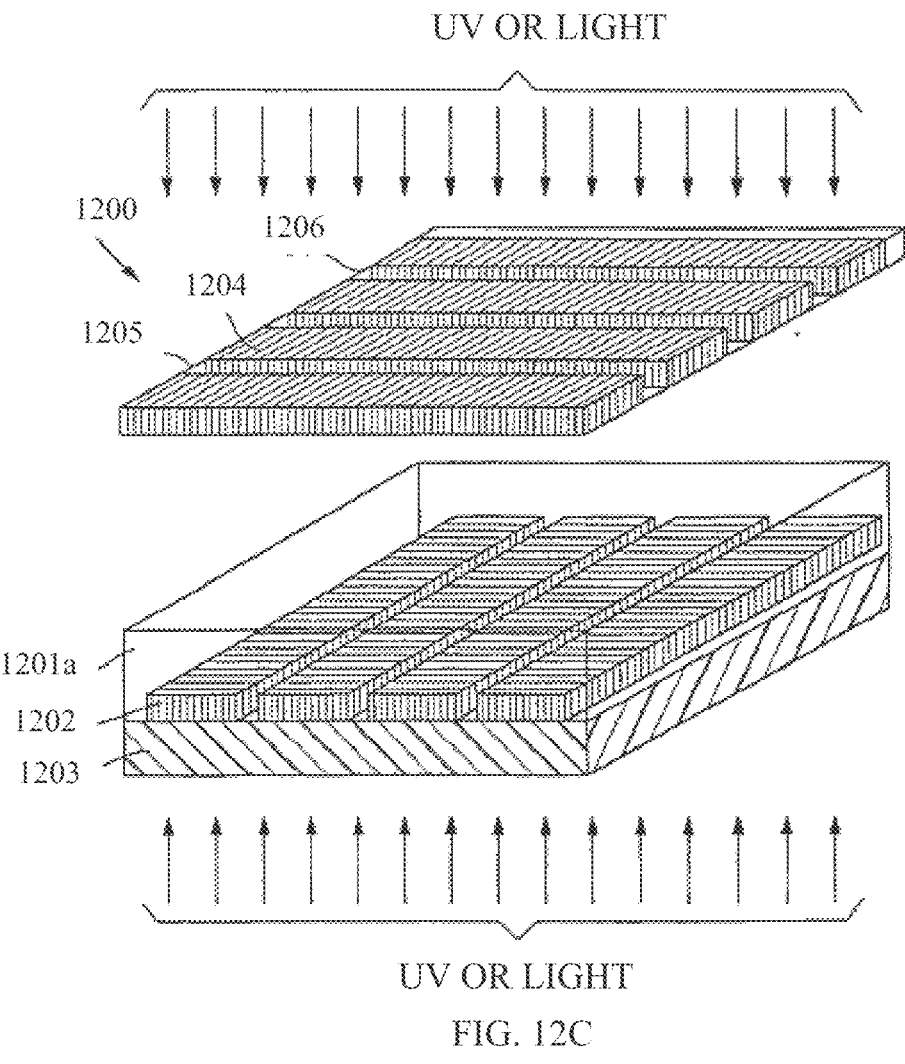
Figure 12D:
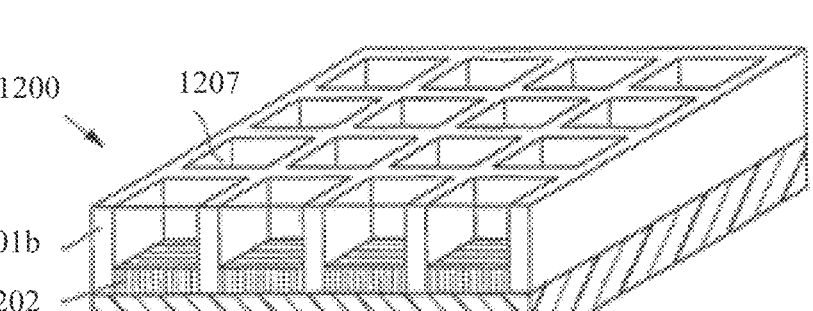

FIGS. 12C and 12D detail an alternate embodiment in which microcells for a fragrance delivery system are fabricated using photolithography. In FIGS. 12C and 12D a combination of top and bottom exposure is used, allowing the walls in one lateral direction to be cured by top photomask exposure, and the walls in another lateral direction to be cured bottom exposure through the opaque base conductor film.

FIGS. 13A-13D illustrate the steps of filling and sealing an array of microcells to be used in a fragrance delivery system.

DETAILED DESCRIPTION

The invention provides a fragrance delivery system whereby fragrances can be released on demand and/or a variety of fragrances can be delivered from the same system at controlled rates, providing a user with the flexibility to deliver customized olfactory effects. The fragrance delivery system of the present invention may be placed or attached on a surface. The fragrance delivery system may be a patch that can be attached on the skin or on the clothes of a person or an animal. The fragrance delivery system may be placed or attached on a surface to provide an olfactory effect in a space. The fragrance delivery system may also be hanged in the desired location to provide an olfactory effect.

The term "fragrance", as used herein, refers to a substance that emits an odor. The fragrance may be a combination of compounds. The compound or compounds that form a fragrance may be natural or synthetic. To provide a desirable olfactory effect, a perfume must have some volatility so that it reaches the smell receptors in the nose of a person.

Typically, the term "perfume" refers to a composition of a fragrance or fragrances and other ingredients. Typically, such compositions also comprise an aqueous or non-aqueous carrier. Herein, we use the term "fragrance composition" referring to such compositions. Fragrance compositions for various products may comprise fragrance modulators and other additives that enhance the effect of a fragrance or fragrances. Herein, fragrance modulators and other additives that enhance the effect of a fragrance or fragrances are classified under the term "fragrance", even in cases that such ingredients are by themselves non-odorous.

"Rate of delivery of a fragrance" from the fragrance delivery system of the present invention and is the amount of the fragrance that is delivered from the fragrance delivery system per unit of time. For example, the rate of delivery may be expressed in units of mg per hour.

A "sealing slice" is a portion of a sealing layer of a fragrance delivery system. A sealing layer of the system may comprise a plurality of sealing slices. A "removable sealing slice" is a portion of a sealing layer that can be completely removed from the fragrance delivery system. A "retractable sealing slice" is a portion of a sealing layer that can be fully or partly retracted from the microcells that are sealed by the slice, resulting in the microcells being opened; in the case of "retractable sealing slice", the slice is not completely removed from the fragrance delivery system.

A "release sheet slice" is a portion of a first release sheet of a fragrance delivery system. A first release sheet of the system may comprise a plurality of release sheet slices. A "removable release sheet slice" is a portion of a first release sheet that can be completely removed from the fragrance delivery system. A "retractable release sheet slice" is a portion of a first release sheet that can be fully or partly retracted from the microcells that are located underneath the release sheet slice, resulting in the microcells being activated; in the case of "retractable release sheet slice", the slice is not completely removed from the fragrance delivery system.

A "top release sheet slice" is a portion of a first release sheet of a fragrance delivery system. A first release sheet of the system may comprise a plurality of release sheet slices. A "removable release sheet slice" is a portion of a first release sheet that can be completely removed from the fragrance delivery system. A "retractable release sheet slice" is a portion of a first release sheet that can be fully or partly retracted from the microcells that are located underneath the release sheet slice, resulting in the microcells being activated; in the case of "retractable release sheet slice", the slice is not completely removed from the fragrance delivery system.

The term "activation of a microcell or a set of microcells or a plurality of microcells" of fragrance delivery system means that the microcell or a set of microcells or a plurality of microcells is in a condition that a detectable quantity of the perfume or the perfumes of the microcell (or in the set of microcells or in the plurality of microcells) can exit the fragrance delivery system.

"Adhesive layer" of the fragrance delivery system is a layer that establishes an adhesive connection between two other layers of the system. An adhesive layer may have thickness of from 200 nm to 5 mm, or from 1 $\mu$m to 100 $\mu$m.

"Porous sealing layer" is a layer of the fragrance delivery system that has average pore size that is larger than 0.2 nm.

"Top coating layer" is a layer of the fragrance delivery system that has average pore size that is larger than 0.1 nm; the pore size of top coating layer is smaller than the pore size of the porous sealing layer.

In one aspect, the present invention provides a fragrance delivery system. The fragrance delivery system comprises a plurality of microcells. Each microcells includes a fragrance composition. The microcells include an opening. The largest dimension of the microcell opening may be from 30 $\mu$m to 5 mm, or from 30 $\mu$m to 500 $\mu$m, or from 80 $\mu$m to 150 $\mu$m. The porous sealing layer spans the opening of each microcell of the plurality of microcells. The plurality of microcells may be loaded with different fragrances (or a combination of fragrances), thereby providing a mechanism to deliver different, or complimentary, fragrances on demand.

Figure 1A:
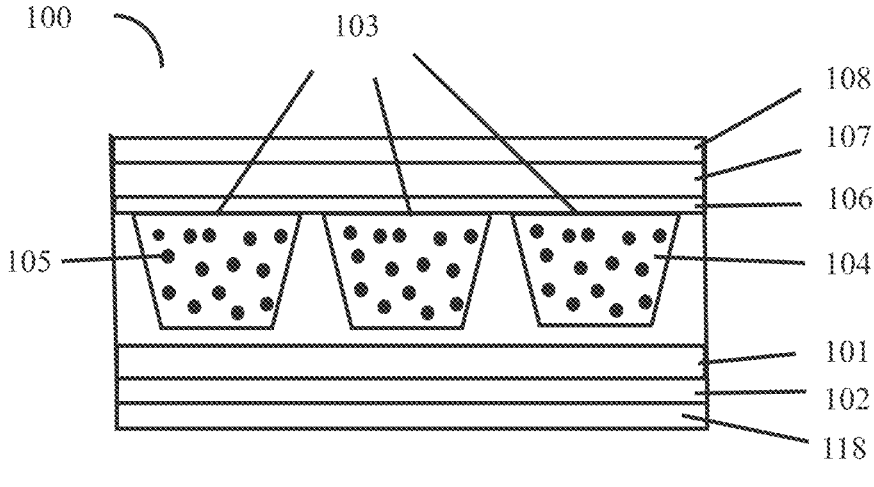
FIG. 1A illustrates a side view of an example of the fragrance delivery system of the present invention that is not attached onto any surface and before activation.

An example of a fragrance delivery system 100 is shown in FIG. 1A. Fragrance delivery system 100 includes a plurality of microcells 103, each microcell including fragrance composition 104. Fragrance composition 104 comprises fragrance 105. Although FIG. 1 shows fragrance 105 as dark dots in fragrance composition 104, implying that fragrance 105 exists in a separate phase, fragrance 105 may be dissolved (in molecular form) in fragrance composition medium 104. Fragrance delivery system 100 illustrated in FIG. 1A comprises backing layer 101 adjacent to the microcell layer. Fragrance delivery system 100 also comprises sealing layer 106, spanning the openings of the plurality of microcells 103. Fragrance delivery system 100 may comprise top coating layer 107 adjacent to sealing layer 106. First release sheet 108 is located adjacent to top coating layer 107. Removal of first release sheet 108 activates the plurality of microcells 103. That is, fragrance 105 may exit microcells 103 and may migrate out of the fragrance delivery system 100, if first release sheet 108 is removed. First release sheet 108 may comprise a plurality of first release sheet slices (not shown in FIG. 1). The plurality of first release sheet slices can be removed or retracted independently from each other. The presence of removable or retractable first release sheet slices enables the user to activate some of the microcells and to leave other microcells not activated at a given time. Fragrance delivery system 100 comprises adhesive layer 101 adjacent to backing layer and a second release sheet 118.

Figure 1B:
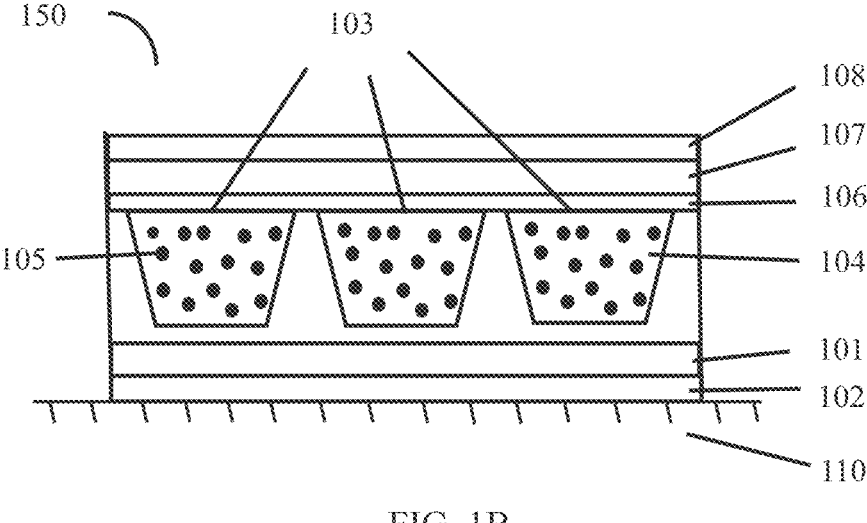
FIG. 1B illustrates a side view of an example of the fragrance delivery system of the present invention that is attached onto a surface before activation.

Second release sheet 118 may be removed from fragrance delivery system 100 and the exposed adhesive layer 102 can be used to securely attach fragrance delivery system onto surface 110 as illustrated in fragrance delivery system 150 of FIG. 1B.

Each microcell is part of an array of microcells that is formed from a polymer matrix, which is described in more detail below. The backing layer of the fragrance delivery system provides structural support and protection against moisture ingress and physical interactions. The backing layer may have thickness of from 1 $\mu$m to 5 mm, or from 25 $\mu$m to 300 $\mu$m.

The microcells are defined by walls that are at least 1 $\mu$m high, although they can be much higher depending upon the desired depth of the microcell. The microcells may be arranged as squares, a honeycomb, circles, etc.

Porous sealing layer 106 may be constructed from a variety of natural or non-natural polymers, such as acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. The porous sealing layer may have thickness of from 500 nm to 3 mm, or from 1 μm to 100 μm.

Removal or retraction of first release sheet 108 of fragrance delivery system 200 activates the corresponding microcells as shown in FIG. 2. This enables fragrance 105 to migrate out of fragrance delivery system 200 through porous sealing layer 106 and top coating layer 107.

Complete removal of first release sheet 108 from fragrance delivery system 200 of FIG. 2 results in fully activated fragrance delivery system 300 shown in FIG. 3A.

The fragrance delivery system of the present invention may comprise first release sheet that comprises a plurality of release sheet slices. Each release sheet slice may be independently removable or retractable. This enables the user of the fragrance delivery system to activate some, and not all the microcells of the fragrance delivery system. The bottom part of FIG. 3B illustrates a side view of fragrance delivery system 350 that is attached onto surface 110. Fragrance delivery system 350 comprises adhesive layer 102, backing layer 101, a microcell layer comprising plurality of microcells 105, porous sealing layer 106, and top coating layer 107. Fragrance delivery system 350 also comprise two release sheet slices 308a and 308b. That is, a number of release sheet slices of the fragrance delivery system 350 have been removed to activate the corresponding microcells. However, fragrance delivery system 350 still comprises two release sheet slices 308a and 308b. The microcells, which are located under the two release sheet slices 308a and 308b, are not activated and can be activated at a future time. The upper part of FIG. 3B illustrates a partial top view of a portion of fragrance delivery system. It shows a plurality of microcells 105 and release sheet slices 308a and 308b. The microcells that are underneath release sheet slices 308a and 308b are not yet activated. Microcells that are located between these not activated microcells are activated, because these microcells do not have release sheet slices above them.

FIG. 4 illustrates fragrance delivery system 400 comprising adhesive layer 402, backing layer 401, a microcell layer comprising a plurality of microcells, porous sealing layer 406, and top coating layer 407. Both porous sealing layer 406 and top coating layer 407 are permeable by fragrance molecules 405. That is, fragrance molecules 405 may migrate through porous sealing layer 406 and top coating layer 407 to be delivered from fragrance delivery system 400 to provide olfactory effects in the nearby space. The average pore size of top coating layer 407 is smaller than the average pore size of sealing layer 408. The first release sheet of the system has been removed. Thus, all microcells of fragrance delivery system 400 are activated. Furthermore, top coating layer 407 has been partially retracted. FIG. 4 illustrates a side view of the system showing three microcells 403a, 403b, and 403c. The structure of fragrance delivery system 400 and the configuration of the porous sealing layer 406 and top coating layer 407 contribute to a different release profile from microcells 403a and 403 b. Specifically, fragrance molecules 405 in microcell 403a, which is covered only by porous sealing layer 406, are delivered at a rate that is higher than that of fragrance molecules 405 of microcells 403b and 403c, which are covered by both porous sealing layer 406 and top coating layer 406, assuming that all three microcells comprise the same fragrance composition.

FIG. 5 illustrates fragrance delivery system 500 comprising adhesive layer 502, backing layer 501, a microcell layer comprising a plurality of microcells, porous sealing layer 506, and top coating layer 507. Both porous sealing layer 506 and top coating layer 507 are permeable by fragrance molecules 505. That is, fragrance molecules 505 may migrate through porous sealing layer 506 and top coating layer 507 to be delivered from fragrance delivery system 500 to provide olfactory effects in the nearby space. The average pore size of top coating layer 507 is smaller than the average pore size of sealing layer 508. The first release sheet of the system has been removed. Thus, all microcells of fragrance delivery system 500 are activated. Furthermore, top coating layer 507 and porous sealing layer has been partially retracted. FIG. 5 illustrates a side view of the system showing three microcells 503a, 503b, and 503c. Microcell 503a is open. That is, there is no porous sealing layer spanning the opening of microcell 503a. Thus, the fragrance comprised in microcell 503a can be delivered from microcell 503a at a high rate of delivery, because the fragrance does not have to migrate through porous sealing layer to exit the fragrance delivery system. On the contrary, the rate of delivery of fragrance 505 from microcells 503b and 503c is lower than rate of delivery from microcell 503a.

FIG. 6 illustrates fragrance delivery system 600 comprising adhesive layer 602, backing layer 601, a microcell layer comprising a plurality of microcells, porous sealing layer 606, and top coating layer 607. Both porous sealing layer 606 and top coating layer 607 are permeable by fragrance molecules 605. That is, fragrance molecules 605 may migrate through porous sealing layer 606 and top coating layer 607 to be delivered from fragrance delivery system 600 to provide olfactory effects in the nearby space. The average pore size of top coating layer 607 is smaller than the average pore size of sealing layer 608. The first release sheet of the system has been removed. Thus, all microcells of fragrance delivery system 600 are activated. FIG. 6 illustrates a side view of the system showing three microcells 603a, 603b, and 603c that contain the same fragrance composition 606. Top coating layer 607 and porous sealing layer have been partially retracted. The result of the partial retraction of top coating layer 607 and porous sealing layer is that microcell 603a is open and microcell 603b is covered by porous sealing layer 606. This means that the rate of delivery of fragrance 605 from microcell 603a is higher than the rate of delivery of fragrance of 605 from microcell 603b, which is higher than the rate of delivery of fragrance 605 from microcell 603c. Microcell 603a is open. That is, there is no porous sealing layer spanning the opening of microcell 603a. Thus, the fragrance comprised in microcell 603a can be delivered from microcell 603a in a high rate of delivery, because the fragrance does not have to migrate through porous sealing layer to exit the fragrance delivery system. On the contrary, the rate of delivery of fragrance 605 from microcells 603b and 603c is lower than rate of delivery from microcell 603a.

The fragrance delivery system of the present invention may comprise different types of microcells, each type of microcells comprising a different fragrance composition. One example of a fragrance delivery system of the present invention is illustrated in FIG. 7. Fragrance delivery system 700 comprises adhesive layer 702, backing layer 701, a microcell layer comprising a plurality of microcells 703, porous sealing layer 706, top coating layer 707, and first release sheet 708. FIG. 7 shows a side view of part of fragrance delivery system 700 having microcells first type of microcells 703a and second type of microcells 703b. First type of microcells 703a comprises a first fragrance composition comprising fragrance 705 and second type of microcells 703b comprises a second fragrance composition comprising fragrance 715, wherein fragrance 705 is different from fragrance 715. The fragrance delivery system may further comprise a third type of microcells comprising a third fragrance composition comprising fragrance F, fragrance F being different from 705 and 715.

The fragrance delivery system of the present invention may comprise different types of microcells, each type of microcells comprising a different fragrance composition. For example, a fragrance delivery system of the present invention may comprise a first type of microcells comprising a composition of fragrance A at concentration C1 and a second type of microcells comprising a composition of fragrance A at concentration C2, wherein C1 is different from C2. The fragrance delivery system may also comprise a third type of microcells comprising a composition of fragrance A at concentration C3, wherein C3 is different from C1 and C2.

The fragrance delivery system of the present invention comprises a plurality of microcells. Each microcell comprises a fragrance composition. The fragrance composition comprises a fragrance or a combination of fragrances. The fragrance composition may further comprise a carrier. The fragrance may be dissolved or dispersed in the carrier. The carrier may be aqueous or non-aqueous. The carrier may be water, optionally comprising a buffer, an organic compound, a combination of organic compounds, or a combination of water and one or more organic compounds. The organic compound may be an alcohol, an ester, an amide, an ether, a carboxylic acid, or other organic compound. The organic compound may be an organic solvent. Non-limiting examples of organic solvents that can be used include DMSO, ethylene glycol, polyethylene glycol, propylene glycol, dipropylene glycol, glycerin, triethyl citrate, ethylene carbonate, and dimethyl carbonate.

The content of the carrier in the fragrance composition may be from 0.01 weight percent to 99 weight percent, or from 0.1 weight percent to 95 weight percent, or from 1 weight percent to 90 weight percent, or from 5 weight percent to 85 weight percent of carrier by weight of the fragrance composition. The fragrance composition may also comprise a polymeric material. In one example, a fragrance composition may comprise a fragrance dispersed in the polymeric material.

The fragrance composition may comprise a carrier from 1 weight percent to 99.99 weight percent by weight of the fragrance composition, or from 5 weight percent to 98 weight percent by weight of the fragrance composition, or from 10 weight percent to 97 weight percent by weight of the fragrance composition, from 25 weight percent to 95 weight percent by weight of the fragrance composition, from 30 weight percent to 92 weight percent by weight of the fragrance composition, or from 40 weight percent to 90 weight percent by weight of the fragrance composition. The fragrance composition may comprise a carrier in a content of more than 10 weight percent, or more than 20 weight percent, or more than 30 weight percent, or more than 40 weight percent, or more than 50 weight percent, or more than 60 weight percent, or more than 70 weight percent, or more than 80 weight percent, or more than 90 weight percent, or more than 95 weight percent, or more than 98 weight percent, or more than 99 weight percent, or more than 99.5 weight percent, or more than 99.9 percent by weight of the fragrance composition.

The fragrance composition may be a liquid. The fragrance composition may be a gel. The same fragrance delivery system may have a first type of microcells comprising a liquid composition and a second type of microcells comprising a gel composition. The first type of microcells may comprise a different fragrance or a different combination of fragrances from the second type of microcells. The first type of microcells may comprise the same fragrance or the same combination of fragrances. The form of the composition in a microcell (aqueous liquid, non-aqueous liquid, gel) may affect the rate of delivery of the corresponding fragrance from the system, especially in the case of an open microcell (having no porous sealing layer, no top coating layer, and no release sheet).

The fragrance delivery system of the present invention may comprise a plurality of microcells. Each of the plurality of microcells has an opening. Each of the plurality of microcells comprises a fragrance composition. The fragrance delivery system comprises a porous sealing layer spanning the openings of the plurality of microcells, the plurality of microcells comprising a plurality of second type of microcells and a plurality of third type of microcells. The portions of the porous sealing layer spanning the openings of the plurality of second type of microcells have a second thickness, the portions of the porous sealing layer spanning the openings of the plurality of third type of microcells have a third thickness. The second thickness is larger than the third thickness. In the case where the average pores of the portions of the porous sealing layer spanning the openings of the plurality of second type of microcells are the same with the portions of the porous sealing layer spanning the openings of the plurality of third type of microcells, the rate of delivery of fragrance from a second type of microcells is lower than the rate of delivery of fragrance from a third type of microcells, because of the thicker portion of the porous sealing layer of the second type of microcells. The plurality of microcells may further comprise a plurality of fourth type of microcells. The portions of the porous sealing layer spanning the openings of the plurality of fourth type of microcells have a fourth thickness. The third thickness is larger than the fourth thickness. In the case where the average pores of the portions of the porous sealing layer spanning the openings of the plurality of fourth type of microcells are the same with the portions of the porous sealing layer spanning the openings of the plurality of third type of microcells and the portions of the porous sealing layer spanning the openings of the plurality of second type of microcells, the rate of delivery of fragrance from a third type of microcells is lower than the rate of delivery of fragrance from a fourth type of microcells, because of the thicker portions of the porous sealing layer of the plurality of third type of microcells.

The fragrance delivery system of the present invention may comprise a plurality of microcells. Each of the plurality of microcells has an opening. Each of the plurality of microcells comprises a fragrance composition. The fragrance delivery system comprises a porous sealing layer spanning the openings of the plurality of microcells, the plurality of microcells comprising a plurality of fifth type of microcells and a plurality of sixth type of microcells. The portions of the porous sealing layer spanning the openings of the plurality of fifth type of microcells have a fifth average pore size, the portions of the porous sealing layer spanning the openings of the plurality of sixth type of microcells have a sixth average pore size. The fifth average pore size is smaller than the sixth average pore size. In the case where the thickness of the portions of the porous sealing layer spanning the openings of the plurality of fifth type of microcells is the same with the portions of the porous sealing layer spanning the openings of the plurality of sixth type of microcells, the rate of delivery of fragrance from a fifth type of microcells is lower than the rate of delivery of fragrance from a sixth type of microcells, because of the smaller average pore size of the porous sealing layer of the fifth type of microcells. The plurality of microcells may further comprise a plurality of seventh type of microcells. The portions of the porous sealing layer spanning the openings of the plurality of seventh type of microcells have a seventh average pore size. The sixth average pore size is smaller than the seventh average pore size. In the case where the thickness of the portions of the porous sealing layer spanning the openings of the plurality of sixth type of microcells is the same with the portions of the porous sealing layer spanning the openings of the plurality of sixth type of microcells and the portions of the porous sealing layer spanning the openings of the plurality of fifth type of microcells, the rate of delivery of fragrance from a sixth type of microcells is lower than the rate of delivery of fragrance from a seventh type of microcells, because of the lower average pore of the portions of the porous sealing layer of the plurality of sixth type of microcells.

FIG. 8 illustrates a side view of a portion of fragrance delivery system 800 comprising adhesive layer 802, backing layer 801, a microcell layer comprising a plurality of microcells including the same fragrance composition 804, porous sealing layer 806, a top coating layer 807, and first release sheet 808. Both porous sealing layer 806 and top coating layer 807 are permeable by fragrance molecules 805. That is, fragrance molecules 805 may migrate through porous sealing layer 806 and top coating layer 807 to be delivered from fragrance delivery system 800 to provide olfactory effects in the nearby space. The openings of the three microcells 803a, 803b, and 803c of fragrance delivery system 800 are sealed by porous sealing layer 806. The portions of sealing layers 806a, 806b, and 806c, spanning the openings of microcells 803a, 803b, and 803c respectively, have different average pore sizes, but the same thickness. The average pore size of portion 806a is smaller than the average pore size of portion 806b, which is smaller than the average pore size of portion 806c. Because of the different average pore size of portions 806a, 806b, and 806c of sealing layer 806, the rate of delivery of fragrance from microcell 803a is lower than the rate of delivery of fragrance from microcell 803b, which is lower than the rate of delivery of fragrance from microcell 803c.

Different porosities of the sealing layer in different microcells can be accomplished by using different polymer materials and microinjection, e.g., using inkjet during the sealing process. Such systems allow a single delivery system to administer varying concentrations of the same or different fragrances over a period of time. For example, a system of the invention may include three types of microcells with a fragrance at three different concentrations. However, the dosage time may be controlled by the porosity of the sealing layer.

Another feature of fragrance delivery system of the present invention that can be used to affect fragrance delivery and the olfactory effect in the surrounding space is the microcell volume. The fragrance delivery system of the present invention comprises a plurality of microcells. The plurality of microcells may comprise a plurality of eighth type of microcells and a plurality of ninth type of microcells. Each microcell of the eighth type of microcells has an eighth volume. Each microcell of the ninth type of microcells has a ninth volume. The eighth volume is larger than the ninth volume. By designing systems having a plurality of different types of microcells with various microcell volumes, the amount of fragrance composition in a microcell can be controlled. Thus, the time and/or duration of the depletion of the fragrance in a microcell in relation to the time and/or duration of the depletion of the fragrance in another microcell provides another tool for the customization of the olfactory effect of the system.

Each microcell of the plurality of microcells may have a volume greater than 0.01 nL, greater than 0.05 nL, greater than 0.1 nL, greater than 1 nL, greater than 10 nL, or greater than 100 nL, or greater than 1 μL, or greater than 10 μL.

Microcells having different volumes is achieved by forming microcells with different depth. The variable microcell depth can be constructed by increasing the amount of polymer at the base of the microcell. This is easily accomplished by using a mold with the desired depth and the embossing technique described below. In other examples, the width of a microcell can be larger or smaller depending upon the volume of solution including a fragrance that is desired to be contained within a given microcell.

FIG. 9 illustrates a side view of a portion of fragrance delivery system 900 comprising adhesive layer 902, backing layer 901, a microcell layer comprising a plurality of microcells including the same fragrance composition 904, porous sealing layer 906, a top coating layer 907, and first release sheet 908. Both porous sealing layer 906 and top coating layer 907 are permeable by fragrance molecules 905. That is, fragrance molecules 905 may migrate through porous sealing layer 906 and top coating layer 907 to be delivered from fragrance delivery system 900 to provide olfactory effects in the nearby space. The microcell layer of fragrance delivery system 900 comprises microcells 903a, 903b, and 903c. As shown in FIG. 9, the volume of microcell 903a is larger than the volume of microcell 903b, which is larger than the volume of microcell 903c. In the case where microcells 903a, 903b, and 903c comprise the same fragrance composition, similar activation of the three microcells at the same time period will result in the depletion of the fragrance in microcell 903c being faster than that of the fragrance from microcells 903a and 903b.

The fragrance delivery system of the present invention may comprise numerous types of microcells. Each type of microcells may comprise a different fragrance. For example, FIG. 10 illustrates fragrance delivery system 1000 having a plurality of four types of microcells 1001, 1002, 1003, and 1004 comprising fragrance compositions, the fragrance compositions comprising Fragrance 1, Fragrance 2, Fragrance 3, and Fragrance 4, respectively. This feature enables the design of sophisticated systems that may provide complex and customized olfactory effects. The arrangement of the different microcell types may not be distributed uniformly across the system. Rather the microcells may be filled in clusters, which makes filling and sealing more straightforward. In other embodiments, smaller microcell arrays may be filled with the same medium, i.e., having the same fragrance at the same concentration, and then the smaller arrays assembled into a larger array to make a delivery system of the invention.

In another aspect, the present invention provides a method of delivering fragrance from a fragrance delivery system.

The fragrance delivery system comprises (a) a backing layer; (b) a microcell layer comprising a plurality of microcells, each microcell of the plurality of microcells having an opening, the plurality of microcells comprising a plurality of first type of microcells, each microcell of the plurality of first type of microcells comprises a composition of a first fragrance having a first concentration of the first fragrance; (c) a porous sealing layer scanning the opening of the plurality of microcells, the porous sealing layer having average pore size of 0.2 nm to 1 mm, the porous sealing layer comprising a plurality of sealing slices, each sealing slice being independently removable or retractable; (d) a top coating layer, the top coating layer having average pore size of less than 0.2 nm, the top coating layer comprising a plurality of top coating slices, each top coating slice being independently removable or retractable; (e) a first release sheet comprising a plurality of release sheet slices, each release sheet slice being independently removable or retractable.

The method of delivering fragrance comprises the steps: (1) removing or retracting the release sheet or one or more release sheet slices; (2) removing or retracting the top coating layer or one or more top coating slices; and (3) removing or retracting the sealing layer or one or more sealing slices.

The method of delivering fragrance may further comprise the step (4) re-attaching the sealing layer or one or more sealing slices.

The method of delivering fragrance may further comprise the step (5) re-attaching the top coating layer or one or more top coating slices.

The method of delivering fragrance may further comprise the step (6) re-attaching the release sheet or one or more release sheet slices.

Techniques for constructing microcells. Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including fragrance delivery and electrophoretic displays. Microcell arrays suitable for use with the invention can be created with microembossing, as illustrated in FIG. 11. A male mold 1100 may be placed either above the web 1104, as shown in FIG. 11, or below the web 1104 (not shown); however, alternative arrangements are possible. See U.S. Pat. No. 7,715,088, which is incorporated herein by reference in its entirety. A conductive substrate may be constructed by forming a conductor film 1101 on polymer substrate that becomes the backing for a device. A composition comprising a thermoplastic, thermoset, or a precursor thereof 1102 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A crosslinkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIG. 11, the mold is released during or after the precursor layer is hardened to reveal an array of microcells 1103. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin, which should have a good release property against the mold surface.

Photolithography. Microcells can also be produced using photolithography. Photolithographic processes for fabricating a microcell array are illustrated in FIGS. 12A and 12B. As shown in FIGS. 12A and 12B, the microcell array 1204 may be prepared by exposure of a radiation curable material 1201*a* coated by known methods onto a conductor electrode film 1202 to UV light (or alternatively other forms of radiation, electron beams and the like) through a mask 1206 to form walls 1201*b* corresponding to the image projected through the mask 1206. The base conductor film 1202 is preferably mounted on a supportive substrate base web 1203, which may comprise a plastic material.

In the photomask 1206 in FIG. 12A, the dark squares 124 represent the opaque area and the space between the dark squares represents the transparent area 1205 of the mask 1206. The UV radiates through the transparent area 1205 onto the radiation curable material 1201*a*. The exposure is preferably performed directly onto the radiation curable material 1201*a*, i.e., the UV does not pass through the substrate 1203 or base conductor 1202 (top exposure). For this reason, neither the substrate 1203, nor the conductor 1202, needs to be transparent to the UV or other radiation wavelengths employed.

As shown in FIG. 12B, the exposed areas 1201*b* become hardened and the unexposed areas (protected by the opaque area 1204 of the mask 1206) are then removed by an appropriate solvent or developer to form the microcells 1207. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Imagewise Exposure. Still another alternative method for the preparation of the microcell array of the invention by imagewise exposure is illustrated in FIGS. 12C and 12D. When opaque conductor lines are used, the conductor lines can be used as the photomask for the exposure from the bottom. Durable microcell walls are formed by additional exposure from the top through a second photomask having opaque lines perpendicular to the conductor lines. FIG. 12C illustrates the use of both the top and bottom exposure principles to produce the microcell array 1200 of the invention. The base conductor film 1202 is opaque and line-patterned. The radiation curable material 1201*a*, which is coated on the base conductor 1202 and substrate 1203, is exposed from the bottom through the conductor line pattern 1202, which serves as the first photomask. A second exposure is performed from the "top" side through the second photomask 1206 having a line pattern perpendicular to the conductor lines 1202. The spaces 1205 between the lines 1204 are substantially transparent to the UV light. In this process, the wall material 1201*b* is cured from the bottom up in one lateral orientation, and cured from the top down in the perpendicular direction, joining to form an integral microcell 1207. As shown in FIG. 12D, the unexposed area is then removed by a solvent or developer as described above to reveal the microcells 1207.

The microcells may be constructed from thermoplastic elastomers, which have good compatibility with the microcells and do not interact with the electrophoretic media. Examples of useful thermoplastic elastomers include ABA, and (AB)n type a di-block, tri-block, and multi-block copolymers wherein A is styrene, α-methylstyrene, ethylene, propylene or norbonene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methylstyrene such as SB (poly(styrene-b-butadiene)), SBS (poly(styrene-b-butadiene-b-styrene)), SIS (poly(styrene-b-isoprene-b-styrene)), SEBS (poly(styrene-b-ethylene/butylenes-b-stylene)) poly (styrene-b-dimethylsiloxane-b-styrene), poly((α-methyl styrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston, Tex.) are particularly useful. Crystalline rubbers such as poly(ethylene-co-propylene-co-5-methylene-2-norbomene) or EDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture, which is immiscible with the display fluid in the microcells and exhibits a specific gravity less than that of the display fluid. Low surface tension solvents are preferred for the overcoating composition because of their better wetting properties over the microcell walls and the electrophoretic fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such as cyclohexane and decalin and the like), alkylbenzenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants front OSi, Greenwich, Conn.) may also be included in the composition to improve the adhesion of the sealant to the microcells and provide a more flexible coating process. Other ingredients including crosslinking agents (e.g., bisazides such as 4,4'-diazidodiphenyl-methane and 2,6-di-(4'-azidobenzal)-4-methylcyclo-hexanone), vulcanizers (e.g., 2-benzothiazolyl disulfide and tetramethylthiuram disulfide), multifunctional monomers or oligomers hexanediol, diacrylates, trimethylolpropane, tria-crylate, divinylbenzene, diallylphthalene), thermal initiators (e.g., dilauroryl peroxide, benzoyl peroxide) and photoinitiators (e.g., isopropyl thioxanthone (ITX), Irgacure 651 and Irgacure 369 from Ciba-Geigy) are also highly useful to enhance the physico-mechanical properties of the sealing layer by crosslinking or polymerization reactions during or after the overcoating process.

After the microcells are produced, they are filled with appropriate mixtures of fragrances. The microcell array 1300 may be prepared by any of the methods described above. As shown in cross-section in FIGS. 13A-13D, the microcell walls 1301 extend upward from the substrate 1003 to form the open cells. The microcells may include a primer layer 1003 to passivate the mixture and keep the microcell material from interacting with the mixture containing the fragrances 1305. Prior to filling, the microcell array 1300 may be cleaned and sterilized to assure that the fragrances are not compromised prior to use.

Figures 13A, 13B, 13C, 13D:
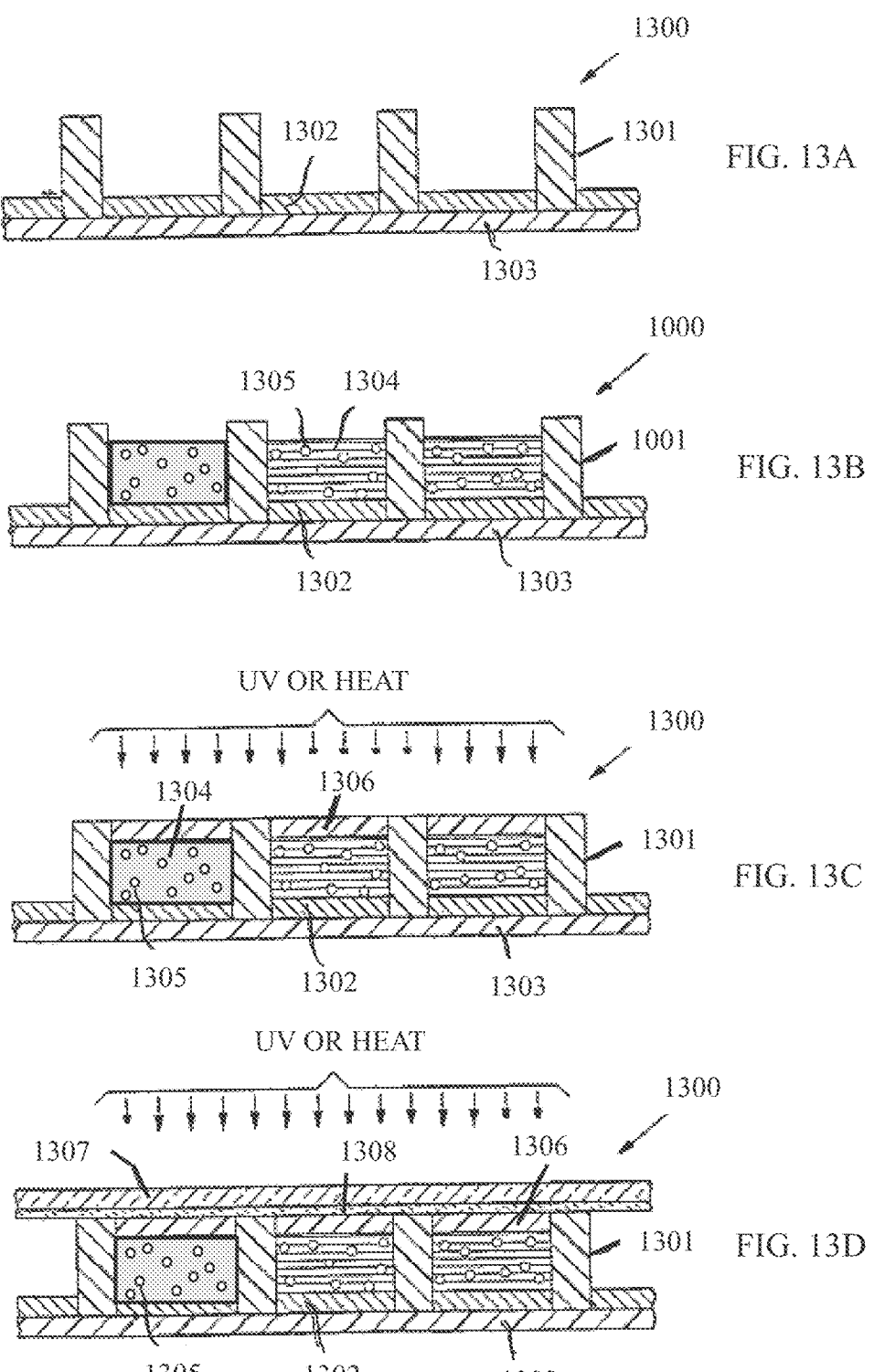

The microcells are next filled with a mixture 1304 including fragrances 1305. The filling of the microcells can be achieved by using picoliter injection with inkjet or other fluidic systems. Individual microcells can be filled to enable a variety of different fragrances to be included in a fragrance delivery system. As shown in FIG. 13B, different microcells may include different fragrances. The microcells 1300 are preferably partially filled to prevent overflow and the unintentional mixing of fragrances. In systems for delivering hydrophobic fragrances, the mixture may be based upon a biocompatible oil or some other biocompatible hydrophobic carrier. For example, the mixture may comprise a vegetable, fruit, or nut oil. In other embodiments, silicone oils may be used. In systems for delivering hydrophilic fragrances, the mixture may be based upon water or another aqueous medium such as phosphate buffer. The mixture need not be a liquid, however, as hydrogels and other matrices may be suitable to deliver the fragrances 1305.

The microcells may be filled using a variety of techniques. In some embodiments, where a large number of neighboring microcells are to be filled with an identical mixture, blade coating may be used to fill the microcells to the depth of the microcell walls 1301. In other embodiments, where a variety of different mixtures is to be filled in a variety of nearby microcell, inkjet-type microinjection can be used to fill the microcells. In yet other embodiments, microneedle arrays may be used to fill an array of microcells with the correct mixtures. The filling may be done in a one-step, or a multistep process. For example, all of the cells may be partially filled with an amount of solvent. The partially filled microcells are then filled with a second mixture including the one or more fragrances to be delivered.

As shown in FIG. 13C, after filling, the microcells are sealed by applying a polymer 66 that becomes the porous sealing layer. In some embodiments, the sealing process may involve exposure to heat, dry hot air, or UV radiation. In most embodiments, the polymer 1306 will be compatible with the mixture 1304 but not dissolved by the solvent of the mixture 1304. The polymer 1306 will also be biocompatible and selected to adhere to the sides or tops of the microcell walls 1301. A suitable biocompatible adhesive for the porous sealing layer is a phenethylamine mixture, such as described in U.S. patent application Ser. No. 15/336,841, filed Oct. 30, 2016 and titled "Method for Sealing Microcell Containers with Phenethyl amine Mixtures," which is incorporated herein by reference in its entirety. Accordingly, the final microcell structure is mostly impervious to leaks and able to withstand flexing without delamination of the porous sealing layer.

In alternate embodiments, a variety of individual microcells may be filled with the desired mixture by using iterative photolithography. The process typically includes coating an array of empty microcells with a layer of positively working photoresist, selectively opening a certain number of the microcells by imagewise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

After the microcells 1300 are filled, the sealed array may be laminated with a finishing layer 1308 that is also porous to the fragrances, preferably by pre-coating the finishing layer 68 with an adhesive layer, which may be a pressure sensitive adhesive, a hot melt adhesive, or a heat, moisture, or radiation curable adhesive. The laminate adhesive may be post-cured by radiation such as MT through the top conductor film if the latter is transparent to the radiation. In some embodiments, a biocompatible adhesive 1307 is then laminated to the assembly. The biocompatible adhesive 1307 will allow fragrances to pass through while keeping the device mobile on a user. Suitable biocompatible adhesives are available from 3M (Minneapolis, MN).

The invention provides for a fragrance delivery system including a plurality of microcells. The microcells include an opening that is spanned by a porous sealing layer. The fragrance delivery system may comprise various types of microcells. The different types of microcells may contain different fragrances or combination of fragrances, different concentration of the same or different fragrances. Different types of microcells may have different porous sealing portion (different thickness, average pore size). Different types of microcells of the same system may have different volume and containing different fragrant composition form (liquid or gel). Significantly, the fragrance delivery system may comprise retractable or removable slices of (a) release sheet, (b) top coating layer, and (c) porous sealing layer. As a result, the rate of delivery of fragrances may be controlled at various levels for each microcell type.

This disclosure is not limiting to the examples and variations that are described, but includes embodiments and other modifications that are self-evident to one of skill in the art.

I claim:

1. A fragrance delivery system comprising:
   a backing layer;
   a microcell layer comprising a plurality of microcells, each microcell of the plurality of microcells having an opening, the plurality of microcells comprising a plurality of first type of microcells, each microcell of the plurality of first type of microcells comprising a composition of a first fragrance having a first concentration of the first fragrance;
   a porous sealing layer spanning the openings of the plurality of microcells, the porous sealing layer having a porous sealing layer average pore size, the porous sealing layer average pore size being from 0.2 nm to 1 mm, the porous sealing layer comprising a plurality of sealing slices, each sealing slice being independently removable or retractable; and
   a first release sheet.

2. The fragrance delivery system of claim 1, wherein the composition of the first fragrance comprises a first aqueous carrier or a first non-aqueous carrier.

3. The fragrance delivery system of claim 2, wherein the composition of the first fragrance is a liquid or a gel.

4. The fragrance delivery system of claim 1, wherein the plurality of microcells comprises a plurality of second type of microcells and a plurality of a third type of microcells, wherein portions of the porous sealing layer span the openings of the plurality of second type of microcells and portions of the porous sealing layer span the openings of the plurality of third type of microcells, wherein the portions of the porous sealing layer spanning the openings of the plurality of second type of microcells have a second thickness, and wherein portions of the porous sealing layer spanning the openings of the plurality of third type of microcells have a third thickness, the second thickness being different from the third thickness.

5. The fragrance delivery system of claim 4, wherein the plurality of microcells further comprises a plurality of fourth type of microcells, wherein portions of the porous sealing layer span the openings of the plurality of fourth type of microcells, and wherein the portions of the porous sealing layer spanning the openings of the plurality of fourth type of microcells have a fourth thickness, the fourth thickness being different from the second thickness and the third thickness.

6. The fragrance delivery system of claim 1, wherein the plurality of microcells comprises a plurality of fifth type of microcells and a plurality of sixth type of microcells, wherein portions of the porous sealing layer span the openings of the plurality of fifth type of microcells and portions of the porous sealing layer span the openings of the plurality of sixth type of microcells, wherein the portions of the porous sealing layer spanning the openings of the plurality of fifth type of microcells have a fifth average pore size, and wherein the portions of the porous sealing layer spanning the openings of the plurality of sixth type of microcells have a sixth average pore size, the fifth average pore size being different from the sixth average pore size.

7. The fragrance delivery system of claim 6, wherein the plurality of microcells comprises a plurality of seventh type of microcells, wherein portions of the porous sealing layer span the openings of the plurality of seventh type of microcells, wherein the portions of the porous sealing layer spanning the openings of the plurality of seventh type of microcells have a seventh average pore size, the seventh average pore size being different from the fifth average pore size and the sixth average pore size.

8. The fragrance delivery system of claim 1, wherein the plurality of microcells comprises a plurality of eighth type of microcells and a plurality of ninth type of microcells, each microcell of the eighth type of microcells having an eighth volume, each microcell of the ninth type of microcells having a ninth volume, the eighth volume being different from the ninth volume.

9. The fragrance delivery system of claim 8, wherein the plurality of microcells comprises a plurality of tenth type of microcells, each microcell of the tenth type of microcells having a tenth volume, the tenth volume being different from the eighth volume and the ninth volume.

10. The fragrance delivery system of claim 1, wherein the plurality of microcells comprises a plurality of eleventh type of microcells and a plurality of twelfth type of microcells, each microcell of the eleventh type of microcells having an eleventh concentration of the first fragrance, each microcell of the twelfth type of microcells having a twelfth concentration of the first fragrance, the eleventh concentration being different from the twelfth concentration.

11. The fragrance delivery system of claim 1, wherein the plurality of microcells further comprises a plurality of thirteenth type of microcells, each microcell of the plurality of thirteenth type of microcells comprises a composition of a second fragrance, the second fragrance being different from the first fragrance.

12. The fragrance delivery system of claim 11, wherein the plurality of microcells further comprises a plurality of fourteenth type of microcells, each microcell of the plurality of fourteenth type of microcells comprises a composition of a third fragrance, the third fragrance being different from the first fragrance and the second fragrance.

13. The fragrance delivery system of claim 1, wherein the release sheet comprises a plurality of release sheet slices, each release sheet slice being independently removable or retractable.

14. The fragrance delivery system of claim 1, further comprising a top coating layer, wherein the top coating layer is disposed between the porous sealing layer and the release sheet, and wherein the top coating layer has a top coating layer pore size, wherein the top coating layer average pore size is larger than 0.1 nm, wherein the top coating average pore size is smaller than the porous sealing layer average pore size, the top coating layer comprising a plurality of top coating slices, each top coating slice being independently removable or retractable.

15. The fragrance delivery system of claim 1, further comprising an adhesive layer adjacent the backing layer, the backing layer being disposed between the adhesive layer and the microcell layer.

16. The fragrance delivery system of claim 15, further comprising a second release sheet adjacent to the adhesive layer, the adhesive layer being disposed between the second release sheet and the backing layer.

17. A method of delivering fragrances form a fragrance delivery system comprising (a) a backing layer; (b) a microcell layer comprising a plurality of microcells, each microcell of the plurality of microcells having an opening, the plurality of microcells comprising a plurality of first type of microcells, each microcell of the plurality of first type of microcells comprising a composition of a first fragrance having a first concentration of the first fragrance; (c) a porous sealing layer scanning the opening of the plurality of microcells, the porous sealing layer having a porous sealing layer average pore size, the porous sealing layer average pore size being from 0.2 nm to 1 mm, the porous sealing layer comprising a plurality of sealing slices, each sealing slice being independently removable or retractable; (d) a top coating layer, the top coating layer having a top coating layer average pore size, the top coating layer average pore size being less than 0.2 nm, the top coating layer comprising a plurality of top coating slices, each top coating slice being independently removable or retractable; (e) a first release sheet comprising a plurality of release sheet slices, each release sheet slice being independently removable or retractable; the method comprising:

(1) removing or retracting the release sheet or one or more release sheet slices;

(2) removing or retracting the top coating layer or one or more top coating slices; and (3) removing or retracting the sealing layer or one or more sealing slices.

18. The method of delivering fragrances according to claim 17, further comprising a step (4) re-attaching the sealing layer or one or more sealing slices.

19. The method of delivering fragrances according to claim 18, further comprising a step (5) re-attaching the top coating layer or one or more top coating slices.

20. The method of delivering fragrances according to claim 19, further comprising a step (6) re-attaching the release sheet or one or more release sheet slices.

* * * * *